United States Patent [19]

Fleet

[11] Patent Number: 5,068,243

[45] Date of Patent: * Nov. 26, 1991

[54] BICYCLIC TETRAHYDROXYPYRROLIZIDINE

[75] Inventor: George W. J. Fleet, Oxford, United Kingdom

[73] Assignee: Monsanto Company, St. Louis, Mo.

[*] Notice: The portion of the term of this patent subsequent to Jun. 18, 2008 has been disclaimed.

[21] Appl. No.: 564,009

[22] Filed: Aug. 7, 1990

Related U.S. Application Data

[63] Continuation-in-part of Ser. No. 404,800, Sep. 8, 1989, Pat. No. 4,992,460, and a continuation-in-part of Ser. No. 524,514, May 17, 1990, Pat. No. 5,021,562.

[51] Int. Cl.$^5$ .................... A61K 31/40; C07D 487/04; C07D 491/22; C07D 493/04
[52] U.S. Cl. ................................. 514/413; 548/423; 548/453; 549/214
[58] Field of Search ................ 548/453, 423; 549/214; 514/413

[56] References Cited

PUBLICATIONS

Fleet et al., J. Chem. Soc., Perkin Trans. 1, 665–666, (1989).
Bashyal et al., Tetrahedron 43, 3083–3093 (1987).
Fleet et al., Tetrahedron 43, 979–990 (1987).
Fleet et al., Tetrahedron Lett., 26, 3127–3131 (1985).
Molyneux et al., Arch. Biochem. Biophys., 251, 450–457 (1986).
Raymond & Vogel, Tetrahedron Lett., 30, 7705–706 (1989).
Setoi et al., Tetrahedron Lett. 26, 4617–4620 (1985).
Hamana et al., J. Org. Chem., 52, 5492–5494 (1987).
Fleet et al., Tetrahedron Lett., 29, 3603–3606 (1988).
Fleet et al., Tetrahedron Lett., 29, 5441–5445 (1988).
Anzeveno et al., J. Org. Chem. 54, 2539–2542 (1989).
Brimacombe and Tucker, Carbohydr. Res. 2, 341–348 (1966).
Stork et al., J. Am. Chem. Soc. 100, 8272–8273 (1978).
Bruce et al., Tetrahedron 46, 19–32 (1990).
Bruce et al., Tetrahedron Lett. 30, 7257–7260 (1989).

Primary Examiner—Mukund J. Shah
Assistant Examiner—Philip I. Datlow
Attorney, Agent, or Firm—Scott J. Meyer; James W. Williams, Jr.

[57] ABSTRACT

Novel bicyclic tetrahydroxylated pyrrolizidines are disclosed which are inhibitors of glycosidase enzymes. A preferred inhibitor is (1S,2R,6R,7S)-1,2,6,7-tetrahydroxypyrrolizidine. It is synthesized from D-glycero-D-talo-heptono-1,4-lactone and utilizes the novel intermediate compounds, 7-O-tert-butyldiphenylsilyl-2,3:5,6-di-O-isopropylidene-D- glycero-D-talo-heptono-1,4-lactone and (1S,2R,6R,7S)-1,2:6,7-di-O-isopropylidene-1,2,6,7-tetrahydroxypyrrolizidine, as follows:

a) reacting D-glycero-D-talo-heptono-1,4-lactone with 2,2-dimethoxypropane to provide a fully protected lactone,
b) selectively removing the acetonide group at C-6,7 to give a C-2,3 protected heptonolactone,
c) reacting the C-2,3 protected lactone with a silyl blocking agent to protect the primary hydroxyl group and give a C-2,3,7 protected lactone,
d) reacting the protected lactone with 2,2-dimethoxypropane to provide a fully protected lactone,
e) reacting the fully protected lactone with fluoride ion to cleave at C7 and thereby provide access to nitrogen in the ring and give a primary alcohol,
f) esterifying the primary alcohol with triflic anhydride to afford a triflate,
g) reacting the triflate with azide ion to give an azidolactone,
h) reducing the azidolactone to give an azidodiol,
i) reacting the azidodiol with methanesulfonyl chloride to provide an axidodimesylate,
j) catalytically hydrogenating the azidodimesylate in ethanol at ambient temperature,
k) heating the resulting product in ethanol in the presence of sodium acetate to give a tetracyclic pyrrolizidine, and
l) removing the acetonide protecting groups of the tetracyclic pyrrolizidine by acid hydrolysis to give (1S,2R,6R,7S)-1,2,6,7-tetrahydroxypyrrolizidine.

5 Claims, No Drawings

BICYCLIC TETRAHYDROXYPYRROLIZIDINE

CROSS-REFERENCE TO RELATED APPLICATION

This is a continuation-in-part of copending application Ser. No. 07/404,800, filed Sept. 8, 1989, now U.S. Pat. No. 4,992,460 and copending application Ser. No. 07/524,514, filed May 17, 1990, now U.S. Pat. No. 5,021,562.

BACKGROUND OF THE INVENTION

This invention relates to novel bicyclic tetrahydroxylated pyrrolizidines and methods for their chemical synthesis. These compounds are useful inhibitors of glycosidase enzymes.

Several naturally occurring polyhydroxylated pyrrolidines, pyrrolizidines and indolizidines are powerful and specific inhibitors of glycosidases [Fellows and Fleet, Alkaloidal Glycosidase Inhibitors from Plants, in Natural Products Isolation (Ed. G. H. Wagman and R. Cooper), Elsevier, Amsterdam, 1988, pp. 540-560; Evans et al, *Phytochemistry* 24, 1953-1956 (1985)]. In recent years, plagiarism of plant chemistry has led to the synthesis of powerful inhibitors of other glycosidases [Fleet et al., *J. Chem. Soc., Perkin Trans.* 1, 665-666, (1989); Bashyal et al, *Tetrahedron* 43, 3083-3093 (1987), and Fleet et al, *Tetrahedron* 43, 979-990 (1987)]. It is now clear that, although changes in stereochemistry of the hydroxyl groups have profound effects on the selectivity of glycosidase inhibition, it is not easy to predict the effects of such changes [Fleet et al, Tetrahedron Lett. 26, 3127-3131 (1985)]. For example, 6-episcastanospermine (A) is a glucosidase inhibitor even though the stereochemistry of the four adjacent chiral centers in the piperidine is similar to those in the pyranose form of mannose [Molyneux et al, *Arch. Biochem. Biophys.* 251, 450-457 (1986)]. Similarly, 1,7a-diepialexine (B), structurally very similar to the powerful mannosidase inhibitor swainsonine (C), is an inhibitor of fungal glucan 1,4-α-glucosidase [Nash et al, Phytochemistry, submitted for publication]. Also, β-C-methyl deoxymannojirimycin (D) is a strong and specific α-L-fucosidase inhibitor and has no effect on human liver α-mannosidase [Fleet et al, *Tetrahedron Lett.*, 30, In Press (1989)].

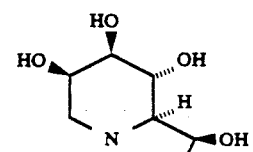

(A)

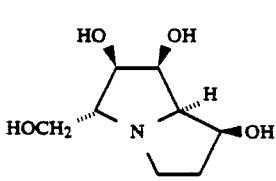

(B)

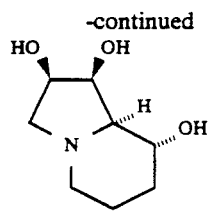

(C)

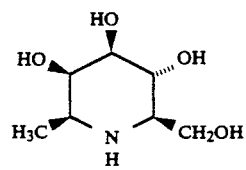

(D)

With a few exceptions [Raymond and Vogel, *Tetrahedron Lett.* 30, 705-706 (1989)], sugars have been the starting materials used in the synthesis of such compounds as castanospermines [such as (A)], Setoi et al, *Tetrahedron Lett.* 26, 4617-4620 (1985), Hamana et al., *J. Org. Chem.* 52, 5492-5494 (1987) and Fleet et al, *Tetrahedron Lett.* 29, 3603-3606 (1988); alexines [such as (B)], Fleet et al, *Tetrahedron Lett.* 29, 5441-5445 (1988); and homonojirimycins [such as (C)]. Anzeveno et al, *J. Org. Chem.* 54, 2539-2542 (1989). Invariably in the syntheses of these compounds with five adjacent chiral centers and six or seven adjacent functional groups, the strategy chosen has been to start from a hexose and to introduce the additional chiral center late in the synthesis. An alternative is to start from derivatives of heptoses, that is by very early introduction of the additional chiral center.

Relatively few studies have been reported on the protecting group chemistry of even readily available heptonolactones [Brimacombe and Tucker, *Carbohydr. Res.* 2, 341-348 (1966)]. Likewise, only a few examples of syntheses from heptose derivatives have been reported. One neat example is described by Stork et al, *J. Am. Chem. Soc.* 100, 8272-8273 (1978). Recently, a research group led by co-inventor Fleet herein has found that suitably protected heptonolactones can be powerful and readily manipulatable chiral pool materials. See Bruce et al, *Tetrahedron* 46, 19-32 (1990); Bruce et al, *Tetrahedron Lett.* 30, 7257-7260 (1989); and copending application Ser. No. 07/524,514, filed May 17, 1990 now allowed, which is a continuation-in-part of application Ser. No. 07/352,068, filed May 15, 1989 now abandoned.

BRIEF DESCRIPTION OF THE INVENTION

In accordance with the present invention, novel bicyclic tetrahydroxylated pyrrolizidines are synthesized from the readily available heptonolactones, D-glycero-D-gulo-heptono-1,4-lactone and the analogous D-glycero-D-talo-heptono-1,4-lactone.

In a preferred embodiment of the invention, the novel (1S,2R,6R,7S)-1,2,6,7-tetrahydroxypyrrolizidine (1) is prepared from D-glycero-talo-heptono-1,4-lactone by a novel twelve step synthesis. This novel tetrahydroxylated pyrrolizidine is an effective inhibitor of human liver glycosidases.

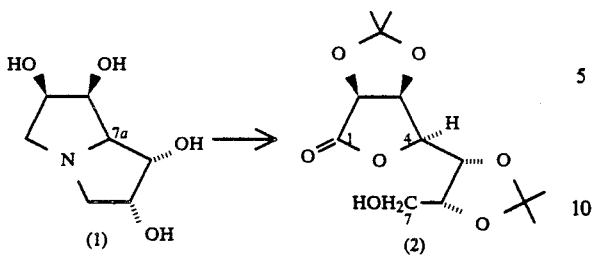

The tetrahydroxypyrrolizidone (1) is an analogue of swainsonine. A similar analogue of 1,8-diepiswainsonine can be made by analogous methods starting with D-glycero-D-gulo-heptono-1,4-lactone to produce the novel (1α,2α,6α,7α,7aβ)-1,2,6,7-tetrahydroxypyrrolizidine.

DETAILED DESCRIPTION OF THE INVENTION

The invention is conveniently illustrated by the following description of the preferred embodiments in which (1S,2R,6R,7S)-1,2,6,7-tetrahydroxypyrrolizidine (1) is synthesized from D-glycero-D-talo-heptono-1,4-lactone (27) in twelve steps as follows in which compound numbers in parentheses correspond to compounds shown by chemical structure herein:

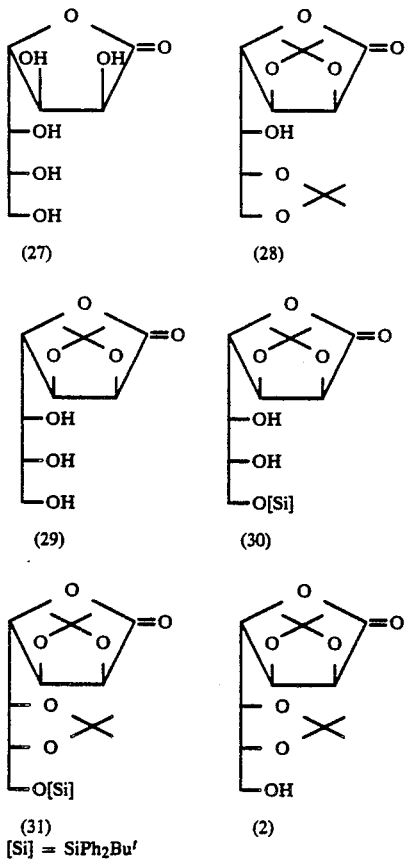

[Si] = SiPh₂Buᵗ

1) The heptonolactone (27) is reacted with 2,2-dimethoxypropane to provide the fully protected lactone or diacetonide (28).

2) The acetonide group at C-6,7 in the diacetonide (28) is selectively removed by acid hydrolysis to give the heptonolactone (29).

3) The primary hydroxyl group in heptonolactone (29) is treated with a silyl blocking agent such as tert-butyldiphenylsilyl chloride to give the protected lactone (30).

4) The protected lactone (30) is reacted with 2,2-dimethoxypropane to provide the fully protected lactone or diacetonide (31).

5) The diacetonide (31) is reacted with fluoride ion to cleave the silyl ether at C7 and thereby provide access to nitrogen in the ring and give the primary alcohol (2).

6) The primary alcohol (2) is esterified with triflic anhydride to afford the triflate.

7) The triflate from step 6 is reacted with azide ion to give the azidolactone (7).

6) The azidolactone (7) is reduced to the azidodiol (8).

9) The azidodiol (8) is reacted with methanesulfonyl chloride to provide the azidodimesylate (9).

10) The azidodimesylate (9) is catalytically hydrogenated in ethanol at ambient temperature.

11) The product from step 10 is heated in ethanol in the presence of sodium acetate to give the tetracyclic pyrrolizidine (10).

12) The acetonide groups in the tetracyclic pyrrolizidine (10) are removed by acid hydrolysis to give the product (1S,2R,6R,7S)-1,2,6,7-tetrahydroxypyrrolizidine (1).

The starting D-glycero-D-talo-heptono-1,4-lactone (27) is a known compound. It can also be readily prepared by the Kiliani reaction on diacetone mannose (25) to give the intermediate 3,4:6,7-di-O-isopropylidene-D-glycero-D-talo-heptono-1,5-lactone (26), followed by acid hydrolysis to cleave the acetonide groups. The synthesis of the intermediate protected heptonolactone (26) also is described in copending application Ser. No. 07/524,514, filed May 17, 1990, which is a continuation-in-part of application Ser. No. 07/352,068, filed May 15, 1989, and by Bruce et al., Tetrahedron Lett. 30, 7257–7260 (1989) and Bruce et al., Tetrahedron 46, 19–32 (1990).

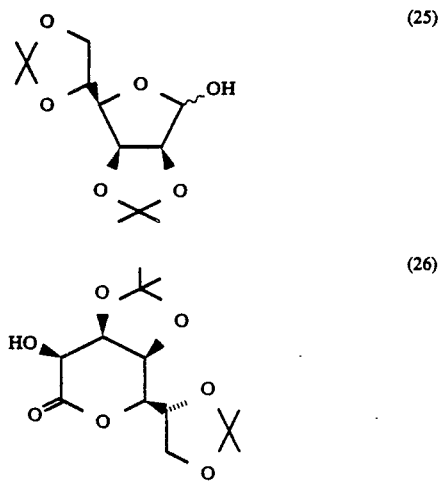

SYNTHESIS OF TETRAHYDROXYPYRROLIZIDINE (1)

The synthesis of homochiral pyrrolizidine (1) requires joining by nitrogen of C-1, C-4 and C-7 of the diacetonide (2). A stereochemical feature of the pyrrolizidine (1), is that it possesses a chirotopic, non-stereogenic center at C-7a and is pseudo $C_2$ symmetric (i.e. the molecule would possess $C_2$ symmetry other than for the center at C-7a). C-7a in (1) is derived from C-4 of the sugar lactone, so that the introduction of nitrogen at this carbon with inversion or retention of configuration will still result in the synthesis of (1). Esterification of the primary alcohol in (2) with trifluoromethanesulphonic anhydride in the presence of pyridine, followed by displacement of the triflate with sodium azide in dimethylformamide, gave the fully protected azide (7) [89% yield]. Reduction of the lactone (7) with sodium borohydride in ethanol afforded the diol (8) [84% yield] which, on treatment with methanesulphonyl chloride in pyridine, was converted to the dimesylate (9) [82% yield]. Hydrogenation of the azide (9) in the presence of palladium black in ethanol gave the corresponding amine which, with sodium acetate, cyclized to the diisopropylidene pyrrolizidine (10) [81% yield]. Removal of the acetonides from (10) with aqueous trifluoroacetic acid gave the target pyrrolizidine (1) in 84% yield [42% overall yield from lactone (2)].

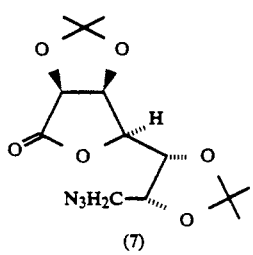

(7)

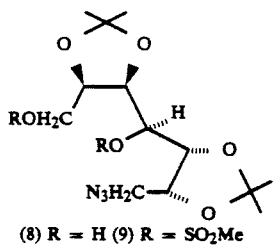

(8) R = H (9) R = SO₂Me

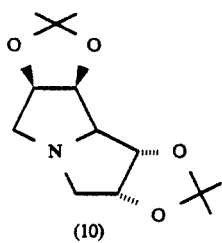

(10)

An alternative approach to the synthesis of the pyrrolizidine (1) can involve initial introduction of azide at C-4 of the sugar, followed by subsequent cyclization of the nitrogen onto leaving groups at C-1 and C-7. Reduction of the silyl ether (11) with sodium borohydride in ethanol gave the diol (12) [86% yield] which with tert-butylchlorodiphenylsilane gave the secondary alcohol (13) [77% yield]. Reaction of (13) with methanesulphonyl chloride in pyridine in the presence of DMAP gave the mesylate (14) [78% yield], suitable for introduction of nitrogen at C-4. Strong confirmatory evidence for the structure of the alcohol (13) was obtained by pyridinium chlorochromate oxidation to the corresponding ketone (15). Both the alcohol (13) and mesylate (14) are pseudo $C_2$ symmetric and have complex $^1H$ and $^{13}C$ NMR spectra; in contrast, the ketone (15) is $C_2$ symmetric with very much simpler NMR spectra.

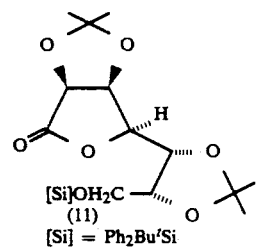

(11)
[Si] = Ph₂Bu'Si

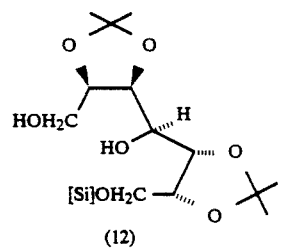

(12)

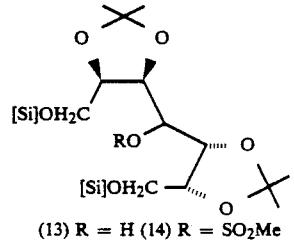

(13) R = H (14) R = SO₂Me

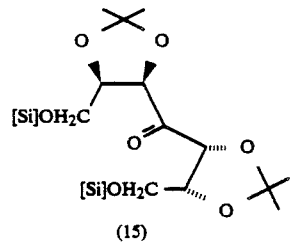

(15)

The symmetry features of compounds such as (13), (14) and (15) can be exploited in two methods of elaboration of the basic carbon skeleton. For acyclic molecules of this symmetry type, the method of two directional chain synthesis has been pioneered by Schrieber, *Chem. Scr.* 27 563 (1987), in the synthesis of precursors of biologically active compounds. However in this case, an alternative strategy of one and two carbon chain extension reactions at the non-stereogenic center would allow the synthesis of analogues of the pyrrolizidine structure, such as (16) and (17), which retain the $C_2$ pseudo symmetry. Furthermore a three carbon chain extension at C-4, coupled with the diasteroselective incorporation of two hydroxyl groups, can provide a synthetic route to (18), an extremely highly functionalized chiral tertiary amine possessing a C3 axis of symmetry. At present there is considerable interest in, and some differing views about the mechanism of, the asymmetric dihydroxylation of olefins by osmium tetroxide in the presence of chiral amines; [Jacobsen et al, *J. Am. Chem. Soc.* 110, 1968, (1988); Wai et al, *J. Am. Chem. Soc.* 111, 1123, (1989); Svendsen et al, *J. Org. Chem.* 54, 2264, (1989); Tomioka et al, *J. Am. Chem. Soc.* 109, 6213 (1987); Tomioka et al, *Tetrahedron Lett.* 29, 573, (1988); Corey et al, *J. Am. Chem. Soc.*, 111, 9243, (1989); Corey et al, *Tetrahedron Lett.* 31, 2665 (1990); Kim et al, *Tetrahedron Lett.* 31, 3003, (1990)]; such bicyclic amines as (1), (16), (17), and (18) may provide interesting probes on the course of this reaction.

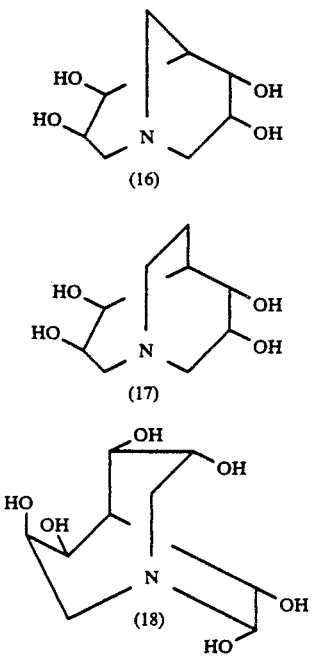

As part of a program to study the effect of polyhydroxylated pyrrolizidines and related compounds as inhibitors of glycosidases, [Collin et al, *Cabohydr. Res.*, 202, 105, (1990)] the effect of the tetrahydroxylated pyrrolizidine (1) on the activity of 15 human liver glycosidases, [Winchester et al, *Biochem. J.* 265, 277, (1990)] was investigated. Although (1) is a moderate inhibitor of α-L-fucosidase (76%) and β-D-galactosidase (53%) at a concentration of 1 mM, it is a very weak inhibitor of the different forms of α-D-mannosidase. This behavior is in marked contrast to the very potent inhibition of these activities by DIM, 1,4dideoxy-1,4-imino-D-mannitol, (19), a nitrogen analogue of the aza-furanose form of mannose. A comparison of the relative inhibitory properties of a series of analogues of (19) and the pyrrolizidine (1) provides some insight into structural features affecting the relative potency of such structures as mannosidase inhibitors (Figure). N-Methylation of DIM, to give (20), [Al Daher et al, *Biochem. J.* 258, 613, (1989)] virtually abolishes inhibition of lysosomal α-D-mannosidase at the enzyme's pH optimum and also greatly decreases the inhibition of other α-mannosidases. The pyrrolizidine (1) is related to DIM (19) by an additional methylene bridge between the ring nitrogen and the carbon bearing the primary hydroxyl function, and is related to N-methyl DIM by elimination of hydrogen between the N-methyl and primary alcohol methylene groups. In contrast, 6-deoxy DIM (20), [Stevens et al., *J. Am. Chem. Soc.* 92, 3160, (1970)] a potent inhibitor of Jack bean α-mannosidase, [Eis et al, *Tetrahedron Lett.* 26, 5397, (1985)] is an even more potent inhibitor of the human liver α-D-mannosidases than is DIM itself; accordingly, it is probable that the loss of freedom in regard to the side chain hydroxyl groups in (1) is an unimportant feature in its lack of glycosidase inhibition. The trihydroxypyrrolizidine (22), [Carpenter et al, *Tetrahedron Lett.* 30, 7261, (1989)] a cyclized analogue of 6-deoxy DIM (20) and a ring contracted form of swainsonine (24), is a better inhibitor of the α-mannosidases than the tetrahydroxylated pyrrolizidine (1); in contrast, the trihydroxypyrrolizidine (23), the C-7 epimer of (22) is inactive towards the enzymes. This behavior parallels the behavior observed in the stereoisomers of swainsonine itself [Cinci de Bello et al, *Biochem. J.* 259, 255 (1989)].

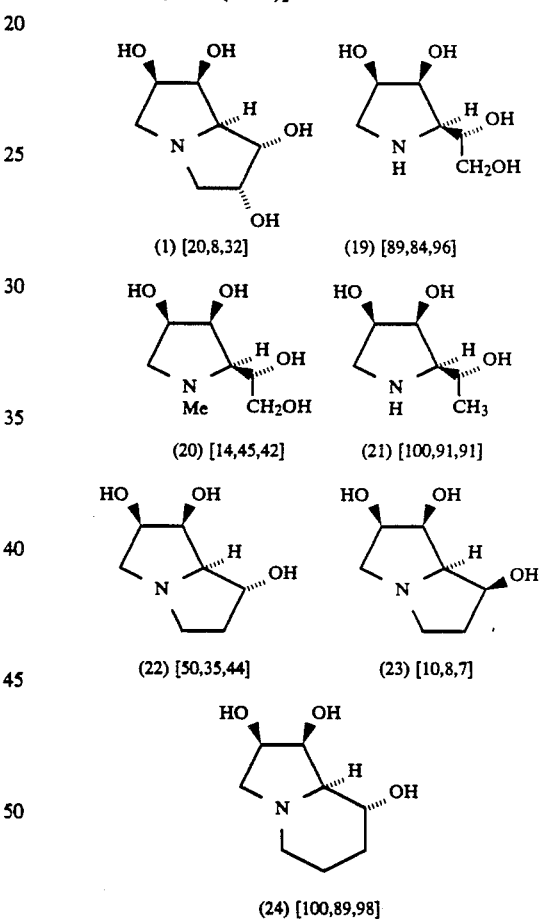

The following examples will further illustrate the invention in greater detail although it will be appreciated that the invention is not limited to these specific examples.

METHODS

Melting points were recorded on a Kofler hot block and are corrected. Proton nuclear magnetic resonance ($\delta_H$) spectra were recorded on Varian Gemini 200 (at 200 MHz), Bruker WH300 (300 MHz), or Bruker WH 500 (500 MHz) spectrometers. $^{13}$C Nuclear magnetic resonance ($\delta_C$) spectra were recorded on a Varian Gemini 200 (50 MHz) spectrometer and multiplicities were assigned using DEPT sequence. $^{13}$C Spectra run in D$_2$O were referenced to methanol ($\delta_C$49.6 ppm) as an internal standard. All chemical shifts are quoted on the δ-scale). Infra-red spectra were recorded on a Perkin-Elmer 781, or on a Perkin-Elmer 1750 FT spectrophotometer. Mass spectra were recorded on VG Micromass 30F, ZAB 1F, Masslab 20–250 or Trio-1 GCMS (DB-5 column) spectrometers using desorption chemical ionization (NH$_3$, DCI) or fast atom bombardment (FAB), as stated. Optical rotations were measured on a Perkin-Elmer 241 polarimeter with a path length of 1 dm. Concentrations are given in g/100 ml. Microanalyses were performed by the microanalysis service of the Dyson-Perrins laboratory. Thin layer chromatography (t.l.c.) was carried out on aluminum sheets coated with 60F$_{254}$ silica or glass plates coated with silica Blend 41. Plates were developed using a spray of 0.2% w/v cerium (IV) sulphate and 5% ammonium molybdate in 2M sulphuric acid or 0.5% ninhydrin in methanol (for amines). Flash chromatography was carried out using Sorbsil C60 40/60 silica. Ion exchange chromatography was carried out with Dowex 50x, 8–100 resin in the H+ form. Solvents and commercially available reagents were dried and purified before use according to standard procedures; dichloromethane was refluxed over and distilled from calcium hydride, methanol was distilled from magnesium methoxide, pyridine was distilled from, and stored over, potassium hydroxide; tetrahydrofuran was distilled, under nitrogen, from a solution dried with sodium in the presence of benzophenone. Hexane was distilled at 68° C. before use to remove involatile fractions.

D-Mannose was obtained from Signa Chemical Company and was converted into 2,3:5,6-di-O-isopropylidene-D-mannofuranose in 80%–90% yield as previously described by Schmidt, *Meth. Carbohydr. Chem.* 2, 318 (1963).

EXAMPLE 1

3,4:6,7-Di-O-isopropylidene-D-glycero-D-talo-heptono-1,5-lactone (26)

and 3,4:6,7-Di-O-isopropylidene-D-glycero-D-galactoheptano-1,5-lactone.

A mixture 2,3:5,6-di-O-isopropylidene-D-mannofuranose (25) (10.8 g, 41.0 mmol), sodium cyanide (1.84 g, 38.0 mmol) and sodium hydrogen carbonate (3 g) in water (200 ml) was stirred at room temperature for 4 days after which time a clear solution was obtained which was free of cyanide. The reaction mixture was then heated at 90° C. for 1.5 h, cooled to room temperature and extracted with dichloromethane (2×20 ml); the dichloromethane layer was dried (sodium sulphate) and the solvent removed to give unreacted starting material (7) (1.84 g, 17%). The aqueous layer was adjusted to pH 3 by dropwise addition of concentrated sulphuric acid and then extracted with ethyl acetate (3×150 ml). The combined ethyl acetate extracts were dried (sodium sulphate) and the solvent removed to give a residue which, after purification by flash chromatography [ethyl acetate:hexane 1:2], gave the following two products, predominantly (26):

A 3,4:6,7-di-O-isopropylidene-D-glycero-D-talo-heptono-1,5-lactone (26)

$R_f$ 0.5 (ethyl acetate:hexane, 2:1) and $R_f$ 0.3 (ethyl acetate:hexane, 1:1), 3.08 g, 26% yield, 31% based on unrecovered starting material), m.p. 157°–159° C. (ethyl acetate:hexane), $[\alpha]_D^{20}$+63.8° (c, 1.3 in CHCl$_3$), $\nu_{max}$ (CHCl$_3$): 3540 (OH), 1767 (C=O) cm$^{-1}$; (Found: C, 54.12; H, 7.09. C$_{13}$H$_{20}$O$_7$ requires: C, 54.16; H, 7.01%.

B 3,4:6,7-di-O-isopropylidene-D-glycero-D-galactoheptono-1,5-lactone $R_f$ 0.7 (ethyl acetate:hexane, 2:1) and $R_f$ 0.6 (ethyl acetate:hexane, 1:1), (0.78 g, 6.6% yield, 8% based on unrecovered starting material), m.p. 140°–141° C. (ether:hexane), $[\alpha]_D^{20}$+93.4° (c, 1.2 in CHCl$_3$), $\nu_{max}$ (CHCl$_3$): 3350 (OH), 1755 (C=O) cm$^{-1}$; (Found C, 54.17; H, 7.25. C$_{13}$H$_{20}$O$_7$ requires: C, 54.16; H, 7.01%).

EXAMPLE 2

2,3:6,7-Di-O-isopropylidene-D-glycero-D-talo-heptono-1,4-lactone (28)

3,4:6,7-Di-O-isopropylidene-D-glycero-D-talo-heptono-1,5-lactone (26) (4.51 g, 15.6 mmol) was stirred at 40° C. in 40% aqueous trifluoroacetic acid (20 ml). Tlc (ethyl acetate) showed immediate consumption of the starting material ($R_f$0.7), production of a major product ($R_f$ 0.3), identified as 3,4-O-isopropylidene-D-glycero-D-talo-heptono-1,5-lactone and also a minor product ($R_f$ 0.1). After 8h, tlc (ethyl acetate) showed a major product ($R_f$ 0.1). The solvent was removed and the residue co-evaporated with toluene (2×10 ml). A small amount of material was purified by flash chromatography (ethyl acetate, increasing polarity to ethyl acetate:ethanol, 9:1) and recrystallised from ethanol-ethyl acetate to give D-glycero-D-talo-heptono-1,5-lactone (27) as a white crystalline solid, m.p. 132°–134° C. [Lit. 131°–132° C.], $[\alpha]_D^{20}$ −35.7° (c, 1.00 in H$_2$O) [Lit. −34.9° (c, 0.6 in H$_2$O)] $\nu_{max}$ (KBr): 3500–3200 (broad, OH), 1770 (C=O) cm$^{-1}$; $\delta_H$ (D$_2$O): 3.50 (3H, m), 3.70 (3H, m), 4.34 (1H, d, H-2, J$_{2,3}$ 5.8 Hz). $\delta_C$(D$_2$O): 63.7 (t, C-7), 69.5, 70.6 (2×d, 2×CHO), 71.1 (d, 2×CHO), 86.6 (d, C-2), 179.8 (s, C-1). m/z (NH$_3$, DCl): 226 (M+NH$_4^+$, 100%), 209 (M+H$^+$, 90%). (Found: C, 40.45 ; H, 5.82. C$_7$H$_{12}$O$_7$ requires: C, 40.39 ; H, 5.81%).

The crude product (27) was dissolved in dry acetone (30 ml). 2,2-Dimethoxypropane (9 ml, 5 equiv) and camphor sulphonic acid (360 mg, 10%) were added and the mixture stirred at room temperature for 24 h. Tlc (ethyl acetate:hexane, 1:1) showed production of a major product ($R_f$ 0.5) which was purified by flash chromatography (ethyl acetate: hexane, 1:3) to give 2,3:6,7-di-O-isopropylidene-D-glycero-D-talo-heptono-1,4-lactone (28) (3.10 g, 69% over two steps) as a colourless viscous oil. $[\alpha]_D^{20}$+29.53° (c, 1.07 in CHCl$_3$), $\nu_{max}$ (film): 3470 (OH), 1773 (C=O) cm$^{-1}$; δH (CDCl$_3$): 1.36 (3H, s, Me), 1.39 (3H, s, Me), 1.41 (3H, s, Me), 1.47 (3H, s, Me), 2.84 (1H, br, OH), 3.87 (1H, br m, H-5), 3.95 (1H, dd, H-7, J$_{6,7}$ 5.8 Hz, J$_{7,7'}$ 8.8 Hz), 4.09 (1H, dd, H-7', J$_{6,7'}$ 6.1 Hz, J$_{7,7'}$ 8.8 Hz), 4.18 (1H, m, H-6), 4.76 (1H, s, H-4), 4.79 (1H, d, H-3, J$_{2,3}$ 5.6 Hz), 4.84 (1H, d, H-2). $\delta_C$(CDCl$_3$): 24.90, 25.29, 26.55, 28.09 (4×q, 4×MeC), 66.09 (t, C-7), 71.59, 74.95, 75.24, 78.82, 82.37 (5×d, 5×CHO), 109.5, 113.2 (2×s, 2×CMe$_2$), 175.73 (s, C-1). m/z (NH$_3$, DCl): 306 (M+NH$_4$+,100%), 289 (M+H+, 90%). This material was unstable as the terminal acetonide was extremely susceptible to hydrolysis.

EXAMPLE 3

2,3-O-Isopropylidene-D-glycero-D-talo-heptono-1,4-lactone (29)

2,3:6,7-Di-O-isopropylidene-D-glycero-D-talo-heptono-1,4-lactone (28) (839 mg, 2.91 mmol), was dissolved in 50% aqueous acetic acid (20 ml), and stirred at room temperature. After 18 h tlc (ethyl acetate) indicated that no starting material remained (R$_f$ 0.8), and a major product had formed (R$_f$ 0.3). The solvent was removed, and the residue purified by flash chromatography (ethyl acetate: hexane, 9:1) to yield 2,3-O-isopropylidene-D-glycero-D-talo-heptono-1,4-lactone (29) (566 mg, 78%) as a white crystalline solid, m.p. 129°-130° C., [α]$_D^{20}$+19.8° (c, 1.00 in MeOH), ν$_{max}$ (KBr): 3400(br, OH), 1800, 1765 (C=O) cm$^{-1}$; δ$_H$ [(CD$_3$)$_2$SO]: 1.29 (3H, s, Me), 1.33 (3H, s, Me), 3.30 (1H, ddd, H-6, J 2.7 Hz, J$_{6,7}$ 5.5 Hz, J 9.0 Hz), 3.5 (2H, m), 4.70 (1H, d, J 5.5 Hz), 4.74 (1H, d, J 5.5 Hz), 4.76 (1H, s). δ$_C$ (CD$_3$OD): 24.98, 26.46 (2×q, 2×MeC), 63.92 (t, C-7), 71.19, 71.30, 76.24, 80.22, 83.34 (5×d, 5×CHO), 113.4 (s, CMe$_2$), 176.96 (s, C-1). m/z (NH$_3$, DCl): 266 (M+NH$_4$+, 100%), 249 (M+H+, 10%). (Found: C, 48.39; H, 6.46. C$_{10}$H$_{16}$O$_7$ requires: C, 48.39: H, 6.50%).

EXAMPLE 4

7-O-tert-Butyldiphenylsilyl-2,3-O-isopropylidene-D-glycero-D-talo-heptono-1,4-lactone (30)

2,3-O-Isopropylidene-D-glycero-D-talo-heptono-1,4-lactone (29) (441 mg, 1.78 mmol) and imidazole (226 mg, 2.2 equiv) were dissolved in dry DMF (5 ml) and stirred at 0° C. under nitrogen. tert-Butylchlorodiphenylsilane (0.51 ml, 1.2 equiv) was added dropwise and the mixture allowed to warm to room temperature. After 2 h tlc (ethyl acetate: hexane, 1:1) indicated the formation of a single product (R$_f$ 0.8). The solvent was removed and the crude reaction mixture shaken with water (20 ml) and ether (10 ml). The aqueous layer was further extracted with ether (3×10 ml), the combined organic extracts were then dried with magnesium sulphate, filtered and the solvent removed. The residue purified by flash column chromatography (ethyl acetate: hexane, 1:3), yielding 7-O-tert-butyldiphenylsilyl-2,3-O-isopropylidene-D-glycero-D-talo-heptono-1,4-lactone (9) (794 mg, 92%) as a white solid, m.p. 40°-44° C. (glassy transition), [α]$_D^{20}$ −7.44° (c, 1.07 in CHCl$_3$), ν$_{max}$(CHCl$_3$): 3450 (broad OH), 1790 (C=O) cm$^{-1}$; δ$_H$ (CDCl$_3$): 1.07 (9H, s, Bu$^t$), 1.40 (3H, s, Me), 1.48 (3H, s, Me), 2.38 (1H, br, s, OH), 3.04 (1H, br, s, OH), 3.84 (4H, m), 4.76 (1H, d, J$_{2,3}$ 5.6 Hz), 4.83 (1H, d, J$_{2,3}$ 5.6 Hz), 4.91 (1H, s), 7.4–7.6 (12H, m, 2×Ph). δ$_C$(CDCl$_3$): 18.99 (SiCMe$_3$), 25.38, 26.60 (2×q, 2×MeC), 26.68 (q, Bu$^t$), 65.84 (t, C-7), 69.26, 73.27, 75.32, 78.94, 82.00 (5×d, 5×CHO), 113.1 (s, CMe$_2$), 127.96, 128.14, 130.31 (3×d, Ph), 175.40 (s, C-1). m/z (NH$_3$, DCl): 504 (M+NH$_4$+, 100%). (Found: C, 64.40; H, 7.28. C$_{26}$H$_{34}$O$_7$Si requires: C, 64.17; H, 7.04%).

EXAMPLE 5

7-O-tert-Butyldiphenylsilyl-2,3:5,6-di-O-isopropylidene-D-glycero-D-talo-heptono-1,4-lactone (31)

7-O-tert-Butyldiphenylsilyl-2,3-O-isopropylidene-D-glycero-D-talo-heptono-1,4-lactone (30) (635 mg, 1.31 mmol) and camphor sulphonic acid (30 mg, 10%) were dissolved in dry acetone (20 ml) and stirred at 50° C. 2,2-Dimethoxypropane (671 mg, 5 equiv) was then added and after 20 min tlc (ethyl acetate: hexane, 1:3) indicated the formation of a single product (R$_f$ 0.7). The reaction mixture was cooled, neutralised with sodium hydrogen carbonate, filtered, the solvent removed and purified by flash column chromatography (ethyl acetate: hexane, 1:5) to yield 7-O-tert -Butyldiphenylsilyl-2,3:5,6-di-O-isopropylidene-D-glycero -D-talo-heptono-1,4-lactone (31) (627 mg, 91%), a white crystalline solid, m.p. 129°-132° C., [α]$_D^{20}$ −25.1° (C., 1.05 in CHCl$_3$), ν$_{max}$(CHCl$_3$): 1790 (C=O) cm$^{-1}$; δ$_H$(CDCl$_3$): 1.08 (9H, s, Bu$^t$), 1.29 (3H, s, Me), 1.34 (3H, s, Me), 1.39 (3H, s, Me), 1.48 (3H, Me), 4.00 (1D, dd, H-7, J$_{6,7}$ 5.6 Hz, J$_{7,7'}$ 10.3 Hz), 4.07 (1H, dd, H-7', J$_{6,7'}$ 10.3 Hz), 4.20 (1H, d, H-5, J$_{5,6}$ 7.3 Hz), 4.42 (1H, ddd, H-6), 4.70 (1H, d, J$_{2,3}$ 5.6 Hz), 4.76 (1H, d), 4.90 (1H, s), 7.4–7.6 (12H, m 2×Ph). δ$_C$ (CDCl$_3$): 19.07 (SiCMe$_3$), 24.36, 25.47, 25.70, 26.63 (4×q, 4×MeC), 26.76 (q, Bu$^t$), 62.47 (t, C-7), 75.22, 76.33, 76.76, 79.17, 79.96 (5×d, 5×CHO), 109.8, 113.2 (2×s, 2×CMe$_2$), 127.98, 130.07, 135.67 (3×d, Ph), 174.6 (s, C-1). m/z (NH$_3$, DCl): 544 (M+NH$_4$+, 100%). (Found: C, 66.02; H, 7.45. C$_{26}$H$_{34}$O$_7$Si requires: C, 66.13; H, 7.27%).

EXAMPLE 6

2,3:5,6-Di-O-isopropylidene-D-glycero-D-talo-heptono-1,4-lactone (2)

7-O-tert-Butyldiphenylsilyl-2,3:5,6-di-O-isopropylidene-D-glycero-D-talo-heptono-1,4-lactone (31) (431 mg, 0.82 mmol) was dissolved in dry THF and stirred at 0° C. under nitrogen. Tetra-n-butylammonium fluoride (0.98 ml, 1M solution in THF, 1.2 equiv) was added dropwise, and after 90 min, tlc (ethyl acetate: hexane, 1:1) indicated the formation of a single product (R$_f$ 0.3, not UV active). Evaporatoin of the solvent produced a yellow oil which was purified by flash chromatography (ethyl acetate: hexane, 1:2) yielding 2,3:5,6-di-O-isopropylidene-D-glycero-D-talo-heptono-1,4-lactone (2) (172 mg, 73%) as a white crystalline solid, m.p. 107°-109° C., [α]$_D^{20}$ −4.8° (c, 1.05 in CHCl$_3$), ν$_{max}$(CHCl$_3$): 3600 ( OH), 1790 (C=O) cm$^{-1}$; δ$_H$(CDCl$_3$): 1.34 (3H, s, Me), 1.37 (3H, s, Me), 1.40 (3H, s, Me), 1.47 (3H, s, Me), 3.86 (1H, dd, H-7, J$_{6,7}$ 5.6 Hz, J$_{7,7'}$ 11.1 Hz), 4.01 (1H, dd, H-7', J$_{6,7'}$ 7.0 Hz), 4.30 (1H, d, J 7.4), 4.46 (1H, ddd, H-6), 4.69 (1H, d, J$_{2,3}$ 5.5 Hz), 4.70 (1H, s, H-3), 4.76 (1H, d). δ$_C$(CDCl$_3$): 24.11, 25.08, 25.66, 26.50 (4×q, 4×MeC), 61.30 (t, C-7) 76.12, 76.87, 78.05, 80.08, 80.99 (5×d, 5×CHO), 109.9, 113.3 (2×s, 2×CMe$_2$), 174.54 (s, C-1). m/z (NH$_3$ DCl): 306 (M+NH$_4$+, 100%), 289(M+H+, 50%). (Found: C, 54.17; H, 7.26. C$_{13}$H$_{20}$O$_7$ requires: C, 54.16; H, 6.99%).

EXAMPLE 7

7-Azido-7-deoxy-2,3:5,6-di-O-isopropylidene-D-glycero-D-talo-heptono-1,4-lactone (7)

2,3:5,6-Di-O-isopropylidene-D-glycero-D-talo-heptono-1,4-lactone (2) (0.21 g, 0.73 mmol) was dissolved in dry dichloromethane (10 ml). Dry pyridine (0.12 ml, 2 equiv), was added and the solution stirred at −30° C., under nitrogen. Trifluoromethanesulphonic anhydride (0.183 ml, 1.5 equiv) was added slowly and the mixture allowed to warm up to room temperature at which point t.l.c.(ethyl acetate: hexane, 1:3) indicated complete product formation (R$_f$ 0.4). The reaction mixture was worked up as quickly as possible. Ice cold brine (10 ml), a drop of dilute hydrochloric acid and a further 10 ml of dichloromethane were added. The layers were separated and the aqueous layer was further extracted with dichloromethane (2×10 ml). The combined organic extracts were then dried with magnesium sulphate, filtered, and the solvent removed to produce an orange residue. Without further purification, this residue was dissolved in dry dimethylformamide (10 ml) and sodium azide (94 mg, 2 equiv based on quantitative triflation) added. The reaction mixture was stirred under nitrogen at room temperature for 12 h when t.l.c. (ethyl acetate: hexane, 1:1) indicated the formation of a single product ($R_f$ 0.8). The solvent was removed, dichloromethane (10 ml) was added, and the resulting solution filtered. The solvent was then removed and the residue purified by flash chromatography (ethyl acetate: hexane, 1:2) to yield 7-azido-7-deoxy-2,3:5,6-Di-O-isopropylidene-D-glycero-D-talo-heptono-1,4-lactone (7) (0.20 g, 89% over 2 steps) as a colourless oil, $[\alpha]_D^{20}$ −38.7° (c, 1.00 in CHCl₃), $\nu_{max}$ (thin film): 2104 (N₃), 1790 (C=O) cm⁻¹; $\delta_H$ (CDCl₃): 1.35 (3H, s, Me), 1.39 (3H, s, Me), 1.41 (3H, s, Me), 1.48 (3H, s, Me), 3.54 (1H, dd, H-7, $J_{6,7}$ 6.1 Hz, $J_{7,7'}$ 12.5 Hz), 3.83 (1H, dd, H-7', $J_{6,7'}$ 7.4 Hz), 4.29 (1H, d, H-5, $J_{5,6}$ 7.4), 4.4–4.5 (1H, m, H-6), 4.66 (1H, s, H-4), 4.70 (1H, d, H-3, $J_{2,3}$ 5.5 Hz), 4.77 (1H, d, H-2). $\delta_C$ (CDCl₃): 24.34, 25.31, 25.83, 26.53 (4×q, 4×MeC), 50.70 (t, C-7), 75.04, 75.27, 75.96, 78.91, 79.45 (5×d, C-2, C-3, C-4, C-5, C-6), 110.17, 113.34 (2×s, 2×CMe₂), 174.17 (s, C-1). m/z (NH₃ DCI): 331 (M+NH₄⁺, 100%), 286(MH⁺-N₂, 90%), 288 (M+NH₄⁺-HN₃, 90%). (Found: C, 49.97H, 6.40N, 13.78. C₁₃H₁₉O₆N₃ requires: C, 49.84; H, 6.11; N, 13.41%).

EXAMPLE 8

7-Azido-7-deoxy-2,3:5,6-di-O-isopropylidene-D-glycero-D-talo-heptitol (8)

7-Azido-7-deoxy-2,3:5,6-di-O-isopropylidene-D-glycero-D-talo-heptono-1,4-lactone (7) (0.29 g, 0.94 mmol) was dissolved in ethanol (20 ml). Sodium borohydride (0.073 g, 2 equiv) was added and the solution stirred at room temperature under nitrogen. After 12 h t.l.c. (ethyl acetate:hexane, 1:1) indicated complete conversion to product ($R_f$ 0.5). The reaction was quenched by addition of an excess of ammonium chloride with effervescence, filtered and the solvent removed to produce a residue that was purified by flash chromatography (ethyl acetate: hexane, 2:3) yielding 7-azido-7-deoxy-2,3:5,6-di-O-isopropylidene-D-glycero-D-talo-heptitol (8) (0.25 g, 84%) as a colourless viscous oil; $[\alpha]_D^{20}$ +3.5° (c, 1.00 in CHCl₃), $\nu_{max}$ (thin film): 3450 (broad OH), 2100 (N₃) cm⁻¹; $\delta_H$ (CDCl₃): 1.37 (3H, s, Me), 1.41(6H, s, 2×Me), 1.42 (3H, s, Me), 3.51 (1H, dd, H-7, $J_{6,7}$ 4.2 Hz, $J_{7,7'}$ 12.6 Hz), 3.67 (1H, dd, H-7', $J_{6,7'}$ 7.4 Hz), 3.78–3.9 (3H, m), 4.14 (1H, dd, J 6.1, 9.6 Hz), 4.34–4.45 (3H, m). $\delta_C$ (CDCl₃): 24.67, 25.85, 26.91, 27.48 (4×q, 4×MeC), 51.45 (t, C-7), 60.47 (t, C-1), 66.92, 75.75, 76.04, 76.72, 77.29 (5×d, C-2, C-3, C-4, C-5, C-6), 108.69, 108.94 (2×s, 2×CMe₂). m/z (NH₃ DCI): 290 (MH⁺-N₂, 100%). (Found: C, 49.50; H, 7.60; N, 13.15%. C₁₃H₂₃N₃O₆ requires: C, 49.20; H, 7.30; N, 13.26%).

EXAMPLE 9

7-Azido-7-deoxy-2,3:5,6-di-O-isopropylidene-1,4-di-O-methanesulphonyl-D-glycero-D-talo-heptitol (9)

7-Azido-7-deoxy-2,3:5,6-di-O-isopropylidene-D-glycero-D-talo-heptitol (8) (0.182 g, 5.7 mmol), and DMAP (1 mg, cat) were dissolved in dry pyridine (8 ml) and stirred at 0° C. under nitrogen. Methanesulphonyl chloride (0.28 ml, 6 equiv), was added slowly and after 4 h the reaction was allowed to warm up to room temperature. After a further 12 h t.l.c. (ethyl acetate: hexane, 2:3) indicated the formation of a major product ($R_f$ 0.4) and also a small amount of a side product ($R_f$ 0.8). The solvent was removed to produce a brown oil which was dissolved in ethyl acetate (15 ml) and washed with water (10 ml). After drying (magnesium sulphate), the solvent was removed to produce a residue which was purified by flash chromatography (ethyl acetate: hexane, 1:2) to afford 7-azido-7-deoxy-2,3:5,6-di-O-isopropylidene-1,4-di-O-methanesulphonyl-D-glycero-D-taloheptitol (9) (0.22 g, 82%) as a colourless viscous oil; $\nu_{max}$ (thin film): 2105 (N₃) cm⁻¹; $\delta_H$ (CDCl₃): 1.37 (3H, s, Me), 1.42 (3H, s, Me), 1.52 (3H, s, Me), 1.59 (3H, s, Me), 3.11 (3H, s, MeSO₂), 3.22 (3H, s, MeSO₂), 3.51 (2H, d, h-7, H-7', J 4.6 Hz), 4.32 (1H, dd, J 5.8, 8.4 Hz), 4.36–4.42 (2H, m), 4.46–4.56 (3H, m), 5.21 (1H, t, J 8.4 Hz). $\delta_C$ (CDCl₃): 24.93, 25.31, 26.39, 27.23 (4×q, 4×MeC), 37.21, 39.31 (2×q, 2×MeSO₂), 51.24 (t, C-7), 68.88 (t, C-1), 74.69, 75.99, 76.30, 76.66, 77.17 (5×d, C-2, C-3, C-4, C-5, C-6), 109.34, 110.18 (2×s, 2×CMe₂). m/z (NH₃ DCI): 446 (MH⁺-N₂, 100%), 491 (M+NH₄⁺, 75%).

EXAMPLE 10

1S,2R,6R,7S-1,2:6,7-Di-O-isopropylidene-1,2,6,7-tetrahydroxypyrrolizidine (10)

7-Azido-7-deoxy-2,3:5,6-di-O-isopropylidene-1,4-di-O-methanesulphonyl-D-glycero-D-talo-heptitol (9) (0.16 g, 3.38 mmol) was dissolved in ethanol (10 ml) and palladium black (10 mg) was added. After degassing the solution, the reaction mixture was stirred vigorously under hydrogen for 15 h when t.l.c. (ethyl acetate:hexane, 1:1) indicated complete formation of a product at the baseline. The reaction mixture was filtered through celite to remove the catalyst, sodium acetate (83 mg, 3 equiv) was added and the mixture stirred at 50° C. under nitrogen. After 24 h t.l.c. (ethyl acetate:methanol, 9:1) indicated complete product formation ($R_f$ 0.4). The solvent was removed and the residue purified by flash chromatography (eluant ethyl acetate, increasing polarity to ethyl acetate: methanol, 9:1) yielding 1S,2R,6R,7S-1,2:6,7-di-O-isopropylidene-1,2,6,7-tetrahydroxy pyrrolizidine (10) (70 mg, 81%) as a pale yellow solid, m.p. 68°-70° C.; $[\alpha]_D^{20}$ −10.0° (c, 1.00 in CHCl₃), $\delta_H$(CDCl₃): 1.29 (3H, s, Me), 1.34 (3H, s, Me), 1.45 (3H, s, Me), 1.54 (3H, s, Me), 3.0 (1H, dd, H-3, $J_{2,3}$ 4.7 Hz, $J_{3,3'}$ 14.4 Hz), 3.17 (1H, d, H-3'), 3.26 (1H, d, H-5, $J_{5,5'}$ 10.9 Hz), 3.42–3.50 (2H, m, H-5', H-7a), 4.66–4.70 (1H, m, H-2), 4.76–4.81 (2H, m, H-1, H-6), 4.94 (1H, d, H-7, $J_{6,7}$ 6.2 Hz). $\delta_C$ (CDCl₃): 22.68, 23.81, 25.77, 26.06 (4×q, 4×MeC), 54.93, 59.22 (2×t, C-3, C-5), 73.8 (d, C-7a), 79.7, 81.6, 81.8, 83.4 (4×d, C-1, C-2, C-6, C-7), 110.72, 111.77 (2×s, 2×CMe₂). m/z (NH₃ DCI): 256 (M+H⁺,100%). (Found: C, 60.96; H, 8.42; N, 5.24%. C₁₃H₂₁NO₄ requires: C, 61.16; H, 8.29; N, 5.49%).

EXAMPLE 11

1S,2R,6R,7S-1,2,6,7-Tetrahydroxypyrrolizidine (1)

1S,2R,6R,7S-1,2:6,7-Di-O-isopropylidene-1,2,6,7-tetrahydroxypyrrolizidine (10) (61 mg, 0.24 mmol) was dissolved in 40% aqueous trifluoroacetic acid and stirred at room temperature for 12 h when t.l.c. (ethyl acetate: methanol, 9:1) indicated complete formation of a single product ($R_f$ 0.1). The solvent was evaporated, the residue dissolved in water and purified by ion exchange chromatography (H+ form), eluting with 0.5M aqueous ammonia. Freeze drying yielded 1S,2R,6R,7S-1,2,6,7-tetrahydroxy pyrrolizidine (1) (34 mg, 84%) as a white solid m.p. 170°–175° C. (decomp), $[\alpha]_D^{20}$ −27.2° (c, 0.965 in H$_2$O), $\nu_{max}$ (KBr) 3500 (br, OH); $\delta_H$ (D$_2$O): 2.51(1H, m, H-3, $J_{3,3'}$ 10 Hz), 2.77 (1H, dd, H-5', $J_{5,5'}$ 12 Hz, $J_{5,6}$ 4 Hz), 3.05–3.13 (2H, m, H-5, H-3) 3.39 (1H, t, H-7a, J 6 Hz), 4.08–4.13 (2H, m, H-1, H-2), 4.19 (1H, m, H-6), 4.34 (1H, dd, H-7, $J_{6,7}$ 4 Hz). $\delta_C$ (CDCl$_3$): 56.2, 59.6 (2×t, C-3, C-5), 70.1, 70.2, 71.3, 73.4, 73.5 (5×d, C-1, C-2, C-6, C-7, C-7a),. m/z (NH$_3$ DCI): 176 (M+H+, 100%). A small portion was then dissolved in water, dilute hydrochloric acid (! ml) was added, the solvent removed and the residue recrystalised from methanol/chloroform to yield the hydrochloride salt of (1), m.p. 127°–129° C. $\delta_C$(CDCl$_3$): 55.5, 60.8 (2×t, C-3, C-5), 69.4, 70.6, 72.5, 72.6, 72.7 (5×d, C-1, C-2, C-6, C-7, C-7a) (Found: C, 34.84, H, 6.64; N, 6.12%. C$_{13}$H$_{21}$NO$_4$(H$_2$O)$_{1.5}$ requires: C, 35.23; H, 6.76; N, 5.87%).

EXAMPLE 12

7-O-tert-Butyldiphenylsilyl-2,3:5,6-di-O-isopropylidene-D-glycero-D-talo-heptitol (12)

7-O-tert-Butyldiphenylsilyl-2,3:5,6-di-O-isopropylidene-D-glycero-D-talo-heptono-1,4-lactone (11)[1] (0.39 g, 0.74 mmol), was dissolved in ethanol (20 ml), sodium borohydride (73 mg, 2 equiv) was added and the mixture was stirred at room temperature for 16 h. At this point t.l.c. (ethyl acetate: hexane, 1:3) indicated complete product formation ($R_f$ 0.2). The reaction was quenched by addition of excess solid ammonium chloride with effervescence. Filtration of the mixture followed by evaporation of the solvent gave a residue which was purified by flash chromatography (eluant ethyl acetate: hexane, 1:5) to yield 7-O-tert-butyldiphenylsilyl-2,3:5,6-di-O-isopropylidene-D-glycero-D-talo-heptitol (12) (0.34 g, 86%), as a colourless viscous oil; $[\alpha]_D^{20}$ −23.6° (c, 1.02 in CHCl$_3$), $\nu_{max}$ (film): 3500 (br, OH) cm$^{-1}$; $\delta_H$(CDCl$_3$): 1.08 (9H, s, Bu$^t$), 1.39 (3H, s, Me), 1.40 (3H, s, Me), 1.41 (3H, s, Me), 1.52 (3H, s, Me), 3.80–3.92 (3H, m), 4.05–4.12 (2H, m), 4.23–4.32 (2H, m), 4.40–4.46 (1H, m), 4.49 (1H, d, J 7 Hz), 7.37–7.50 (6H, m, ArH), 7.66–7.75 (4H, m, ArH). $\delta_C$ (CDCl$_3$): 19.0 (SiCMe$_3$), 24.7, 25.11, 26.47, 27.74 (4×q, 4×MeC), 26.63 (q, $^t$Bu), 60.7 (t, C-1), 62.1 (t, C-7), 67.5, 75.8, 76.5, 77.6, 77.7 (5×d, C-2, C-3, C-4, C-5, C-6), 108.5 (s, 2×CMe$_2$), 128.0, 130.2, 135.7 (3×d, ArC), 132.7 (s, ArC). m/z (NH$_3$, DCI): 395 (M+H+-[$^t$Bu+Ph], 100%), 531 (MH+). (Found: C, 65.13; H, 8.43. C$_{29}$H$_{42}$O$_7$Si requires: C, 65.63; H, 7.98%).

EXAMPLE 13

1,7-Di-O-tert-butyldiphenylsilyl-2,3:5,6-di-O-isopropylidene-D-glycero-D-talo-heptitol (13)

7-O-tert-Butyldiphenylsilyl-2,3:5,6-di-O-isopropylidene-D-glycero-D-talo-heptitol (12) (0.28 g, 0.52 mmol) and imidazole (77 mg, 2.2 equiv) were dissolved in dry dimethylformamide (8 ml) and stirred at 0° C. under nitrogen. tert-Butylchlorodiphenylsilane (0.16 ml, 1.2 equiv) was added dropwise and the reaction mixture allowed to warm up to room temperature. After 4 h t.l.c. (ethyl acetate: hexane, 1:3) indicated complete product formation ($R_f$ 0.7). The solvent was removed and the crude reaction mixture partitioned between water (20 ml) and ether (15 ml). The layers were separated and the aqueous layer further extracted with ether (2×15 ml). The combined organic extracts were washed with brine (3×10 ml), dried (magnesium sulphate) and filtered. Evaporation of the solvent followed by flash chromaptography (dichloromethane: hexane, 3:1 increasing polarity to neat dichloromethane) yielded 1,7-di-O-tert-butyldiphenylsilyl-2,3:5,6-di-O-isopropylidene-D-glycero-D-talo-heptitol (13) (0.305 g, 77%) as a colourless viscous oil; $[\alpha]_D^{20}$ − 10.9° (c, 1.01 in CHCl$_3$), $\nu_{max}$ (film): 3500 (br, OH) cm$^{-1}$; $\delta_H$(CDCl$_3$): 1.01, 1.02 (18H, 2×s, 2×$^t$Bu), 1.34 (3H, s, Me), 1.35 (3H, s, Me), 1.37 (3H, s, Me), 1.50 (3H, s, Me), 3.37 (1H, d, OH, J 5.2 Hz), 3.75 (1H, dd, J 11 Hz, 6 Hz), 3.90–4.09 (4H, m), 4.19–4.45 (4H, m), 7.29–7.43 (12H, m, ArH), 7.64–7.68 (8H, m, ArH). $\delta_C$ (CDCl$_3$): 19.0 (SiCMe$_3$), 25.0, 25.4, 27.9 (q, 4×MeC), 26.7 (q, 2×$^t$Bu), 62.9 (t, C-1, C-7), 67.1, 76.2, 76.7 (d, C-2, C-3, C-4, C-5, C-6), 108.5 (s, 2×CMe$_2$), 127.8, 129.9, 135.7 (3×d, ArC), 133.2, 133.3 (2×s, ArC). m/z (NH$_3$, DCI): 691 (M+-$^t$Bu), 711 (M+-Ph), 769 (M+H+), 786 (M+NH$_4$+). (Found: C, 70.35; H, 7.74. C$_{45}$H$_{60}$O$_7$Si$_2$ requires: C, 70.27; H, 7.86%).

EXAMPLE 14

1,7-Di-O-tert-butyldiphenylsilyl-2,3:5,6-di-O-isopropylidene-4-O-methanesulphonyl-D-glycero-D-taloheptitol (14)

1,7-Di-O-tert-butyldiphenylsilyl-2,3:5,6-di-O-isopropylidene-D-glycero-D-talo-heptitol (13) (90 mg, 0.12 mmol) was dissolved in dry pyridine (5 ml) and stirred at 0° C. under nitrogen. Methanesulphonyl chloride (0.06 ml, 6 equiv) and 4-(N,N-dimethylamino)-pyridine (1 mg) were added and the mixture allowed to warm up to room temperature. After 24 h, t.l.c. (ethyl acetate: hexane, 1:3) indicated the formation of a single product ($R_f$ 0.6). The solvent was removed and the residue shaken with water (10 ml) and ether (10 ml). The layers were separated and the aqueous layer further extracted with ether(2×10 ml). The combined organic extracts were then dried (magnesium sulphate), filtered and the solvent removed. The residue was then purified by flash chromatography (eluant ethyl acetate: hexane, 1:5) to yield 1,7-di-O-tert-butyldiphenylsilyl-2,3:5,6-di-O-isopropylidene-4-O-methanesulphonyl-D-glycero-D-talo-heptitol (14) (77 mg, 78%) as a yellow white solid m.p. 32°–35° C.; $\delta_H$ (CDCl$_3$): 1.07, 1.11 (18H, 2×s, 2×$^t$Bu), 1.28 (3H, s, Me), 1.29 (3H, s, Me), 1.36 (3H, s, Me), 1.42 (3H, s, Me), 2.97 (3H, s, MeSO$_2$), 3.69–3.98 (3H, m), 4.17–4.26 (2H, m), 4.37–4.56 (3H, m), 5.27 (1H, dd, H-4, J 3.2, 7.5 Hz), 7.38–7.42 (12H, m, ArH), 7.69–7.76 (8H, m, ArH). $\delta_C$ (CDCl$_3$): 19.0, 19.1 (2×s, 2×SiCMe$_3$), 25.22, 25.51, 27.13 (q, 4×MeC), 26.72 (q, 2×$^t$Bu), 39.16 (q, MeSO$_2$), 62.44, 63.36 (2×t, C-1, C-7), 75.77, 77.62, 78.27, 78.27, 78.46 (5×d, C-2, C-3, C-4, C-5, C-6), 108.33, 108.87 (2×s, 2×CMe$_2$), 127.87, 129.87, 135.8 (3×d, 3×ArC), 129.86 (s, ArC). m/z (FAB, NaOAc): 847 (MH+), 869 (M+Na+, 100%).

EXAMPLE 15

1,7-Di-O-tert-butyldiphenylsilyl-2,3:5,6-di-O-isopropylidene-D-manno-hept-4-ulose (15)

1,7-Di-O-tert-butyldiphenylsilyl-2,3:5,6-di-O-isopropylidene-D-glycero-D-talo-heptitol (13) (200 mg, 0.26 mmol), powdered molecular sieve (300 mg) and pyridinium chlorochromate (168 mg, 3 equiv) were stirred at room temperature in dry dichloromethane (8 ml) under nitrogen for 24 h. Ether (15 ml) was then added and the mixture filtered through a silica plug (ether eluant) topped with celite. The solvent was then removed to leave a crude product which was purified by flash chromatography (ethyl acetate: hexane, 1:9) to yield 1,7-di-O-tert-butyldiphenylsilyl-2,3:5,6-di-O-isopropylidene-D-manno-hept-4-ulose (15), (159 mg, 80%) as a colourless viscous oil; $\nu_{max}$ (film): 1744 (C=O) cm$^{-1}$; $\delta_H$ (CDCl$_3$): 1.10 (18H, s, 2×Bu$^t$), 1.27 (6H, s, 2×Me), 1.55 (6H, s, 2×Me), 3.76 (4H, d, J 6.2 Hz, H-1, H-1', H-7, H-7'), 4.44–4.54 (2H, m, H-2, H-6), 5.15 (2H, d, J 7 Hz, H-3, H-5), 7.36–7.44 (12H, m, ArH), 7.69–7.73 (8H, m, ArH). $\delta_C$(CDCl$_3$): 19.0 (SiCMe$_3$), 25.4, 26.5 (q, 4×MeC), 26.8 (q, 2×CMe$_3$), 62.6 (t, C-1, C-7), 78.4, 80.2 (2×d, C-2, C-3, C-5, C-6), 110.4 (s, 2×CMe$_2$), 127.9, 130.0, 135.8 (3×d, ArC), 133.0 (s, ArC). m/z (NH$_3$, DCI): 784 (M+NH$_4^+$).

Various other examples will be apparent to the person skilled in the art after reading the present disclosure without departing from the spirit and scope of the invention. It is intended that all such other examples be included within the scope of the appended claims.

What is claimed is:

1. (1S,2R,6R,7S)-1,2,6,7-tetrahydroxypyrrolizidine.

2. The method of inhibiting a glycosidase enzyme in a biological fluid containing said enzyme comprising subjecting said fluid to an effective amount of the compound of claim 1 suitable to inhibit said glycosidase.

3. A method for the production of (1S,2R,6R,7S)-1,2,6,7-tetrahydroxypyrrolizidine comprising:

a) reacting D-glycero-D-talo-heptono-1,4-lactone with 2,2-dimethoxypropane to provide a fully protected lactone, b) selectively removing the acetonide group at C-6,7 to give a C-2,3 protected heptonolactone, c) reacting the C-2,3 protected lactone with a silyl blocking agent to protect the primary hydroxyl group and give a C-2,3,7 protected lactone, d) reacting the protected lactone with 2,2-dimethoxypropane to provide a fully protected lactone, e) reacting the fully protected lactone with fluoride ion to cleave at C7 and thereby provide access to nitrogen in the ring and give a primary alcohol, f) esterifying the primary alcohol with triflic anhydride to afford a triflate, g) reacting the triflate with azide ion to give an azidolactone, h) reducing the azidolactone to give an azidodiol, i) reacting the azidodiol with methanesulfonyl chloride to provide an azidodimesylate, j) catalytically hydrogenating the azidodimesylate in ethanol at ambient temperature, k) heating the resulting product in ethanol in the presence of sodium acetate to give a tetracyclic pyrrolizidine, and l) removing the acetonide protecting groups of the tetracyclic pyrrolizidine by acid hydrolysis to give (1S,2R,6R,7S)-1,2,6,7-tetrahydroxypyrrolizidine.

4. 7-O-tert-Butylidiphenylsilyl-2,3:5,6-di-O-isopropylidene-D-glycero-D-talo-heptono-1,4-lactone.

5. (1S,2R,6R,7S)-1,2:6,7-di-O-isopropylidene-1,2,6,7-tetrahydroxypyrrolizidine.

* * * * *